United States Patent [19]

Sohn et al.

[11] Patent Number: 5,426,203

[45] Date of Patent: Jun. 20, 1995

[54] PLATINUM COMPLEXES OF MALONIC ACID DERIVATIVES AND PROCESS FOR THE PREPARATION THEREOF

[75] Inventors: Youn S. Sohn; Ok S. Jung; Young A. Lee; Kwan M. Kim, all of Seoul, Rep. of Korea

[73] Assignee: Korea Institute of Science and Technology, Seoul, Rep. of Korea

[21] Appl. No.: 178,674

[22] Filed: Jan. 7, 1994

[30] Foreign Application Priority Data

Oct. 16, 1993 [KR] Rep. of Korea ............... 21558/1993

[51] Int. Cl.$^6$ ............................................. C07F 15/00
[52] U.S. Cl. ...................................................... 556/137
[58] Field of Search ......................................... 556/137

[56] References Cited

U.S. PATENT DOCUMENTS 5,142,075  8/1992  Sohn et al. ........................ 556/137

OTHER PUBLICATIONS

*Nature*, Feb. 13, 1965, vol. 205, pp. 698–699, by B. Rosenberg, entitled "Inhibition of Cell Division in Escherichia Cell by Electrolysis Products from a Platinum Electrode".

*Biochimie*, 1978, vol. 60, pp. 825–850, by M. J. Cleare, entitled "Anti-Tumor Platinum Compexes: Relationships Between Chemical Properties and Activity".

*Inorganic Chimica Acta*, vol. 46, 1980, pp. L15–L16, by R. C. Harrison and C. A. McAuliffe, entitled "An Efficient Route for the Preparation of Highly Soluble Platinum (II) Antitumor Agents".

*Can. J. Chem.*, vol. 64, 1894, (Revised 1986) pp. 1894–1896, by F. D. Rochon and P. C. Kong, entitled "Iodo–Bridged Complexes of Platinum(II) and Synthesis of cis Mixed–Amine Platinum (II) Compounds".

*Telbahedron*, vol. 29, (1973) pp. 635–638, by W. Lehnert, entitled: "Knoevenagel-Kondensationen mit TiCl$_1$/BASE—III$^1$".

*European Journal, Cancer*, vol. 7, (1981) pp. 129–141 by Abraham Goldin et al, entitled: "Current Results of the Screening Program at the Division of Cancer Treatment, National Cancer Institute".

Primary Examiner—José G. Dees
Assistant Examiner—Porfirio Nazario-Gonzalez
Attorney, Agent, or Firm—Lowe, Price, LeBlanc & Becker

[57] ABSTRACT

Novel platinum complexes wherein malonate derivative is the anion ligand are provided with processes for preparation thereof. The complexes of the present invention have excellent antitumor effect and low toxicity.

1 Claim, No Drawings

PLATINUM COMPLEXES OF MALONIC ACID DERIVATIVES AND PROCESS FOR THE PREPARATION THEREOF

SUMMARY OF THE INVENTION

The present invention relates to platinum complexes with excellent antitumor activity represented by the following general formula I and processes for the preparation thereof.

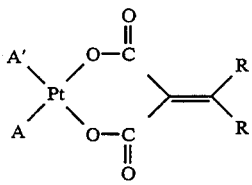

wherein A and A' are same or different from each other and selected from the group consisting of ammonia($NH_3$), methylamine($CH_3NH_2$), ethylamine($C_2H_5NH_2$), n-propylamine(n-$C_3H_7NH_2$), isopropylamine(iso-$C_3H_7NH_2$), cyclopropylamine(cyclo-$C_3H_5NH_2$), cyclobutylamine(cyclo-$C_4H_7NH_2$), cyclopentylamine(cyclo-$C_5H_9NH_2$), and cyclohexylamine(cyclo-$C_6H_{11}NH_2$) or optionally, these two amine groups combine together to form a chelating amine such as ethylenediamine($NH_2CH_2CH_2NH_2$), trans($\pm$)-1,2-diaminocyclohexane(trans($\pm$)-1,2-($NH_2$)$_2$-cyclo-$C_6H_{10}$), trans(1R,2R)-1,2-diaminocyclohexane(trans(1R,2R)-1,2-($NH_2$)$_2$-cyclo-$C_6H_{10}$), 2,2-dimethyl-1,3-propanediamine($NH_2CH_2C(CH_3)_2CH_2NH_2$), 1,1-cyclobutanedimethaneamine(1,1-cyclo-$C_4H_6(CH_2NH_2)_2$), 1,1-cyclopentanedimethaneamine(1,1-cyclo-$C_5H_8(CH_2NH_2)_2$), 1,1-cyclohexanedimethaneamine(1,1-cyclo-$C_6H_{10}(CH_2NH_2)_2$), tetrahydro-4H-pyran-4,4-dimethaneamine($O(CH_2CH_2)_2C(CH_2NH_2)_2$), or 1,4-diamino-2-butanol($NH_2CH_2CH_2CH(OH)CH_2NH_2$): R is methyl, ethyl, of propyl or, optionally, these two R groups combine together to form propylene(—$CH_2CH_2CH_2$—), butylene(—$CH_2(CH_2)_2CH_2$—), or pentylene(—$CH_2(CH_2)_3CH_2$—).

It has been found by the present inventors that the platinum complexes containing these anions as provided in the present invention are novel compounds exhibiting excellent antitumor activity which have not known yet.

BACKGROUND OF THE INVENTION

Since the discovery of antitumor activity of cisplatin, i.e., cis-($NH_3$)$_2PtCl_2$ by B. Rosenberg (Nature, 205,698 (1965)), comprehensive studies including its clinical tests have been performed leading to FDA approval of cisplatin as a chemotherapeutic antitumor agent in 1979. Currently, cisplatin is one of the most widely used antitumor agents and, in particular, is effective for testicular, ovarian, bladder, lung, bone marrow, and larynx cancers, but because of its high toxicity ($LD_{50}=13$ mg/kg, M. J. Cleare, Biochimie, 60, 835(1978)), its use is limited. On the other hand, carboplatin, i.e., cis-($NH_3$)$_2$Pt(CBDCA)(CBDCA=1,1-cyclobutanedicarboxylate) which was approved by FDA in 1989, has much lower toxicity ($LD_{50}=180$ mg/kg, M. J. Cleare, Biochimie, 60 (1978)) compared with cisplatin, but its antitumor activity is lower and more expensive than cisplatin. Therefore, a great deal of researches for searching new antitumor agents having a higher antitumor activity and lower toxicity than those of cisplatin or caroplatin is actively underway.

With a view to develop novel platinum antitumor agents having a higher antitumor effect and lower toxicity than those of cisplatin, the present inventors modified the molecular structure of anion and nuetral amine ligand of cisplatin to synthesize new platinum complexes and examined the physiological activity thereof. As a result, the present inventors has found that the platinum complexes bound by a malonic acid derivative containing a double bond at α-position exhibited an excellent antitumor activity and filed an application for the malonic acid derivatives platinum complexes containing sulfur atom as Korean patent application No. 91-11401 filed Jul. 5, 1991 (the corresponding U.S. application has been granted as the U.S. Pat. No. 5,142,075) wherein A=A'=$NH_3$, $CH_3NH_2$, $C_2H_5NH_2$, iso-$C_3H_7NH_2$, cyclo-$C_3H_5NH_2$, AA'=$NH_2CH_2CH_2NH_2$, 1,2-($NH_2$)$_2$-cyclo-$C_6H_{10}$, $CH(OH)(CH_2NH_2)_2$; RR=—SCHCHS—, $SCH_2CH_2S$-, R=$SCH_3$). The present inventors have continued the studies and found that the platinum complexes represented by the formula I containing malonic acids without sulfur of the following general formulas II-A and II-B as anion group have superior antitumor activity to that of carboplatin and cisplatin and much lower toxicity than that of cisplatin. Moreover, the compounds of formula I of the present invention exhibit an improved water-solubility. Thus, it is possible to solve the problems as troubled in the use of cisplatin due to the low water-solubility.

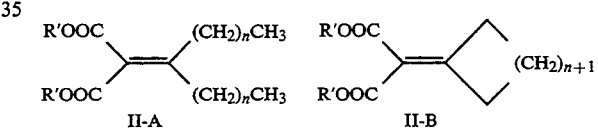

DETAILED DESCRIPTION OF THE INVENTION

The compounds of the present invention as represented by the formula I can be prepared, for example, according to the following procedure.

The esters of dicarboxylic acid of formula II is refluxed in the presence of alkali to obtain alkali metal salts of formula III and then the obtained salts are reacted with barium chloride to form barium salts of formula IV. It is also possible to react esters of dicarboxylic acid with barium hydroxide to directly obtain barium salts of formula IV.

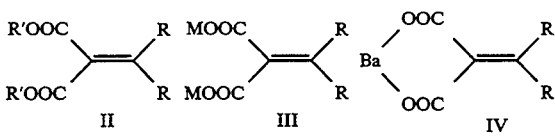

wherein R' is ethyl or isopropyl; R is defined as previously as in formula I and; M is ammonium, sodium or potassium.

Then, either of the alkali metal salts of formula III or the barium salts of the formula IV are reacted with an amine-platinum intermediate such as platinum nitrate derivative of formula V or platinum sulfate derivative of formula VI, respectively, to obtain the subject platinum complexes of formula I.

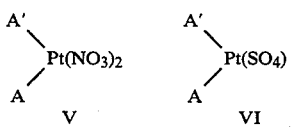

wherein A and A' are defined as previously as in formula I.

The platinum nitrate derivatives of formula V or platinum sulfate derivatives of formula VI are prepared by reacting amineplatinum iodides of formula VII with silver nitrate and silver sulfate, respectively, in water solvent for 4 hours as taught by R. C. Harrison (*Inorg. Chimica Acta*, 46, L15(1980)).

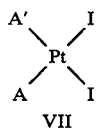

wherein A and A' are defined as previously as in formula I.

The amineplatinum iodide VII wherein A and A' are same can be easily obtained by reacting potassium tetrachloro platinate and potassium iodide and corresponding amine compounds according to M. J. Cleare (*Biochimie*, 60, 835(1978)). Meanwhile, the amineplatinum iodide VII wherein A and A' are different from each other is obtained by reacting the above-obtained amineplatinum iodide wherein A and A' are same with perchloric acid to prepare iodine-bridge bonded dimer, followed by reacting with other kind of amine, according to F. D. Rochon (*Can. J. Chem.*, 64, 1894(1986)).

The detailed description of the process for the preparation of the subject compounds are as herebelow. The anion group, malonic acid derivative of formula II-A and II-B which forms the key structure of the compounds of the formula I is obtained by condensating dialkylketone such as acetone, diethylketone, and dipropylketone, or cyclic ketone such as cyclobutanone, cyclopentanone, and cyclohexanone with malonic acid ethylester or malonic acid isopropylester in the solution of tetrahydrofuran (THF) in the presence of TiCl$_4$/CCl$_4$ catalyst in accordance with W. Lehnert (Tetrahedron 29, 635(1973)).

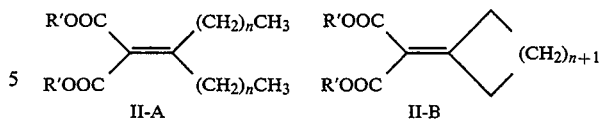

wherein R' is ethyl or isopropyl and n is an integer from 0 to 2.

Dicarboxylic acid esters of formula II as obtained above are hydrolyzed to be reacted with amineplatinum intermediates at aqueous phase. In other words, dicarboxylic acid ester of formula II is stirred in the solvent of ethanol at the room temperature in the presence of 2.0 to 2.2 equivalents of alkali such as KOH or NaOH for 5 to 20 hours to precipitate the aqueous alkali salt of formula III. The obtained salt is filtered, washed and then used as such in the synthesis of platinum complex, or it is reacted with equivalent barium chloride to be converted to barium salts of formula IV. Alternatively, dicarboxylic acid esters of formula II is stirred with reflux in aqueous solution for 5–7 hours in the presence of 1.0 to 1.2 equivalents of barium hydroxide(Ba(OH)$_2$.8H$_2$O), then cooled to the room temperature(25° C.) followed by concentration under reduced pressure (3–10 mmHg) with saturated solution, and added by same volume of methanol to directly precipitate the barium salts of formula IV. Depending on the solubility of the final compounds of formula I, alkali salts of formula III or barium salts of formula IV are reacted with amineplatinum nitrate of formula V or amineplatinum sulfate of formula VI in aqueous solution to obtain pure platinum complexes of formula I. For example, if the final platinum complex is slightly soluble in water, the aqueous solution of alkali salt III is mixed with aqueous solution of amineplatinum nitrate V or aqueous solution of amineplatinum sulfate VI and then concentrated to obtain the platinum complex as precipitate while the nitrate or sulfate of alkali is dissolved in water. On the other hand, if the final product is soluble in water, barium salt IV and amineplatinum sulfate VI are reacted in an aqueous solution. As the insoluble barium sulfate is quantitatively precipitated, it can be simply removed. Then, the filtrate is just concentrated, or followed by addition of organic solvent such as acetone or alcohol to obtain platinum complex I in crystalline or powdery form due to its reduced solubility.

The aforementioned procedure for the preparation of the platinum complexes according to the present invention may be summarized as in the following reaction scheme.

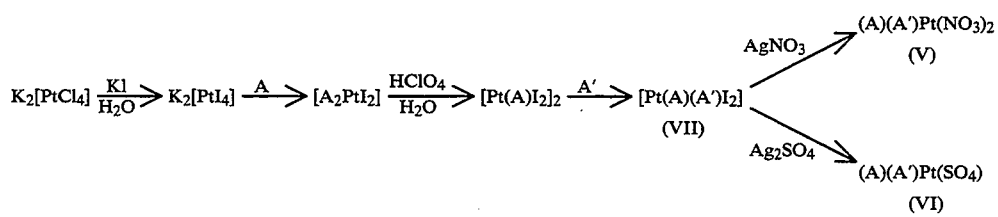

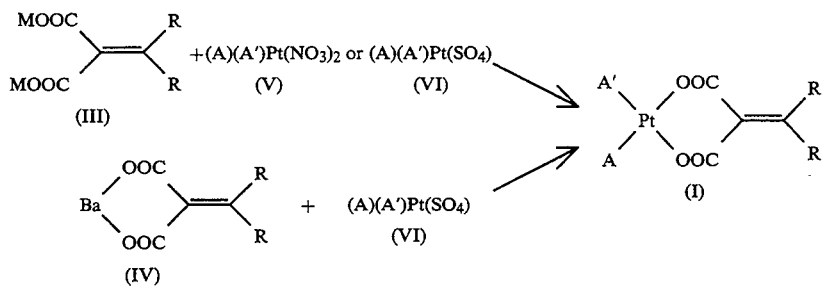

The following examples are given by way of illustration and are not to be construed as limiting the invention in any way inasmuch as many variation of the invention are possible within the spirit of the invention.

The elementary analysis of the platinum complexes of the present invention was carried out by using Perkin Elmer C,H,N analyzer. The Infrared Absorption spectrum was measured by Model 101025 FT-IR of MIDAC Co., U.S.A. in the range of 4000–400 cm$^{-1}$.

EXAMPLE 1

Preparation of $(NH_3)_2Pt(OOC)_2C=C(CH_3)_2 (A=A'=NH_3; R=CH_3)$

To a solution of 5.00 g (25 mmol) malonic acid derivative, $(CH_3)_2C=C(COOC_2H_5)_2$ in 50 ml water, 100 ml of aqueous solution of 9.46 g (30 mmol) of $Ba(OH)_2.8-H_2O$ was added and then refluxed with stirring for 5 hours to hydrolyze. The reactant was cooled to the room temperature (25° C.). After removing the small amount of the precipitate, the filtrate was concentrated under reduced pressure (3 mmHg) to 20 mL. The same volume of methanol was added to stand at low temperature (−5° C.) for 2 hours to obtain white solid precipitate. The obtained precipitate was filtered and washed for two times with methanol and ethylether, respectively, and then dried under reduced pressure (3 mmHg) to obtain 7.25 g (92% yield) of barium salt $[(CH_3)_2C=C(COO)_2Ba].2H_2O$.

To the solution of 0.95 g (3.00 mmol) of the resulted $[(CH_3)_2C=C(COO)_2Ba].2H_2O$ dissolved in 100 mL of water, gradually added an aqueous solution of $(NH_3)_2PtSO_4$ which had been obtained by reacting 1.45 g (3.00 mmol) of amine-platinum intermediate $(NH_3)_2PtI_2$ with 0.94 g (3.0 mmol) of $Ag_2SO_4$ and stirred for 2 hours. After filtering the precipitate, the filtrate was concentrated under reduced pressure (3 mmHg) to 20 mL to obtain white crystalline powder. The resulted precipitate was filtered, and dried under reduced pressure (3 mmHg) at the room temperature (25° C.) to obtain 0.99 g (89.2% yield) of platinum complex, $(NH_3)_2Pt(OOC)_2C=C(CH_3)_2$ of the following properties:

m.p.: 165° C. (decomp.) Elemental Analysis (%) for $(C_6H_{12}N_2O_4)Pt$ Found: C, 19.2; H, 3.20; N, 7.32 Calcd.: C, 19.4; H, 3.25; N, 7.54 IR bands (KBr;cm$^{-1}$); 683(m), 797(m), 860(m), 1107(m), 1348(s), 1447(m), 163(s), 3231(s), 3468(m)

EXAMPLE 2

Preparation of

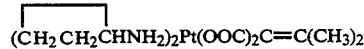

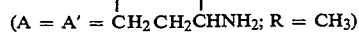

Following the procedure of Example 1 and using the same equivalent of cyclopropylamine instead of ammonia, the platinum complex of

was obtained in 72.7% yield.

m.p.: 126° C. (decomp.) Elemental Analysis (%) for $(C_{12}H_{20}N_2O_4)Pt(H_2O)$ Found: C, 30.9; H, 4.07; N, 5.62 Calcd.: C, 30.7; H, 4.72; N, 5.96 IR bands (KBr;cm$^{-1}$); 704(m), 812(s), 932(m), 1020(m), 1111(m), 1285(sh), 1437(sh), 1606(s), 1640(s) 2917(m), 3090(s), 3179(s), 3497(m)

EXAMPLE 3

Preparation of $(i-C_3H_7NH_2)_2Pt(OOC)_2C=C(CH_3)_2(A=A'=i-C_3H_7NH_2; R=CH_3)$ Following the procedure of Example 1 and using the same equivalent of isopropylamine instead of ammonia, the platinum complex of $(i-C_3H_7NH_2)_2Pt(OOC)_2C=C(CH_3)_2].H_2O$ was obtained in 75.3% yield. m.p.: 119° C. (decomp.) Elemental Analysis (%) for $(C_{12}H_{24}N_2O_4)Pt(H_2O)$ Found: C, 30.1; H, 5.33; N, 5.86 Calcd.: C, 30.4; H, 5.54; N, 5.92 IR bands (KBr;cm$^{-1}$); 706(m), 812(m), 935(m), 1115(m), 1273(m), 1368(s), 1588(s), 1644(s), 2973(m), 3084(s), 3196(s), 3420(m)

EXAMPLE 4

Preparation of $(NH_2CH_2CH_2NH_2)_2Pt(OOC)_2C=C(CH_3)_2(A\widehat{A}'=NH_2CH_2CH_2NH_2; R=CH_3)$ Following the procedure of Example 1 and using the same equivalent of ethylenediamine instead of ammonia, the platinum complex of $[(NH_2CH_2CH_2NH_2)_2Pt(OOC)_2C=C(CH_3)_2].H_2O$ was obtained in 82.5% yield.

m.p.: 192° C. (decomp.) Elemental Analysis (%) for $(C_8H_{14}N_2O_4)Pt(H_2O)$ Found: C, 22.8; H, 3.31; N, 6.70 Calcd.: C, 23.1; H, 3.88; N, 6.75 IR bands (KBr;cm$^{-1}$); 812(m), 1065(m), 1248(m), 1364(s), 1431(m), 1564(s), 1620(s), 1665(s), 3055(s), 3221(s), 3426(m)

EXAMPLE 5

Preparation of

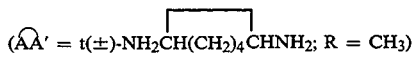

Following the procedure of Example 1 and using the same equivalent of trans($\pm$)-1,2-diaminocyclohexane instead of ammonia, the platinum complex of

was obtained in 81.6% yield.

m.p.: 182° C. (decomp.) Elemental Analysis (%) for $(C_{12}H_{20}N_2O_4)Pt(H_2O)$ Found: C, 31.0; H, 4.27; N, 5.75 Calcd.: C, 30.7; H, 4.72; N, 5.96 IR bands (KBr;cm$^{-1}$); 706(m), 814(s), 930(m), 1109(m), 1177(m), 1346(s), 1447(sh), 1611(s), 1640(s), 2934(s), 3092(s), 3214(s), 3466(m)

EXAMPLE 6

Preparation of
$[NH_2CH_2C(CH_3)_2CH_2NH_2]Pt(OOC)_2C=C(CH_3)_2$ ($\overset{\frown}{AA}'=NH_2CH_2C(CH_3)_2CH_2NH_2$; R=CH$_3$)

Following the procedure of Example 1 and using the same equivalent of 2,2-dimethyl-1,3-diaminopropane instead of ammonia, the platinum complex of $\{[NH_2CH_2C(CH_3)_2CH_2NH_2]Pt(OOC)_2C=C(CH_3)_2\}\cdot 2H_2O$ was obtained in 87.0% yield.

m. p.: 164° C. (decomp.) Elemental Analysis (%) for $(C_{11}H_{20}N_2O_4)Pt(2H_2O)$ Found: C, 27.7; H, 5.35; N, 5.95 Calcd.: C, 27.8; H, 5.09; N, 5.89 IR bands (KBr;cm$^{-1}$); 702(m), 810(s), 1034(m), 1113(m), 1175(m), 1387(s), 1443(sh), 1466(s), 1599(s), 2922(m), 3119(s), 3177(s), 3364(s)

EXAMPLE 7

Preparation of

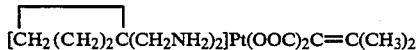

Following the procedure of Example 1 and using the same equivalent of 1,1-cyclobutanedimethaneamine instead of ammonia, the platinum complex of

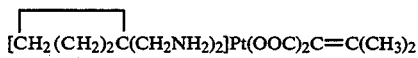

was obtained in 80.6% yield.

m.p.: 179° C. (decomp.) Elemental Analysis (%) for $(C_{12}H_{20}N_2O_4)Pt$ Found: C, 31.5; H, 4.78; N, 5.80 Calcd.: C, 31.9; H, 4.46; N, 6.21 IR bands (KBr;cm$^{-1}$); 816(m), 1013(m), 1107(m), 1321(s), 1370(s), 1445(m), 1570(s), 1645(s), 2951(s), 3219(s), 3426(s)

EXAMPLE 8

Preparation of

Following the procedure of Example 1 and using the same equivalent of 1,1-cyclopentanedimethaneamine instead of ammonia, the platinum complex of

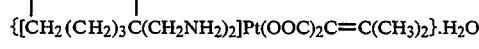

was obtained in 87.1% yield.

m.p.: 187° C. (decomp.) Elemental Analysis (%) for $(C_{13}H_{22}N_2O_4)Pt(H_2O)$ Found: C, 36.7; H, 5.06; N, 5.75 Calcd.: C, 36.7; H, 5.39; N, 5.35 IR bands (KBr;cm$^{-1}$); 812(m), 1017(m), 1111(m), 1350(s), 1445(m), 1607(s), 2872(m), 2947(m), 3069(m), 3216(m), 3287(m), 3443(m)

EXAMPLE 9

Preparation of

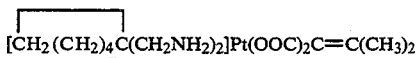

Following the procedure of Example 1 and using the same equivalent of 1,1-cyclohexanedimethaneamine instead of ammonia, the platinum complex of

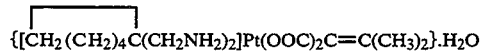

was obtained in 83.8% yield.

m.p.: 218° C. (decomp.) Elemental Analysis (%) for $(C_{14}H_{24}N_2O_4)Pt(H_2O)$ Found: C, 33.8; H, 4.62; N, 6.03 Calcd.: C, 33.8; H, 5.27; N, 5.63 IR bands (KBr;cm$^{-1}$); 702(m), 818(m), 1103(m), 1227(m), 1345(s), 1368(sh), 1451(m), 1650(s), 2861(m), 2930(m), 3297(m)

EXAMPLE 10

Preparation of
$[O(CH_2CH_2)_2C(CH_2NH_2)_2]Pt(OOC)_2C=C(CH_3)_2$ ($\overset{\frown}{AA}'=O(CH_2CH_2)_2C(CH_2NH_2)_2$; R=CH$_3$)

Following the procedure of Example 1 and using the same equivalent of tetrahydro-4H-pyran-4,4-dimethaneamine instead of ammonia, the platinum complex of $[O(CH_2CH_2)_2C(CH_2NH_2)_2]Pt(OOC)_2C=C(CH_3)_2$ was obtained in 84.5% yield.

m.p.: 172° C. (decomp.) Elemental Analysis (%) for $(C_{13}H_{22}N_2O_5)Pt$ Found: C, 32.1; H, 4.53; N, 5.72 Calcd.: C, 32.4; H, 4.60; N, 5.82 IR bands (krBr;cm$^{-1}$); 700(m), 818(m), 1024(m), 1100(m), 1227(m), 1325(s), 1366(sh), 1451(m), 1618(s), 1644(s), 2847(m), 2913(m), 3129(m), 3233(s), 3397(m)

EXAMPLE 11

Preparation of

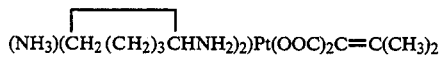

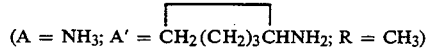

2.90 g (6 mmol) of (NH$_3$)$_2$PtI$_2$ was suspended in 150 mL of distilled water and 30 mL of 0.67M aquous perhydrochloric acid solution was added thereto and stirred in boiled water bath at 45° C. for 48 hours. The color of the precipitate was changed from yellow to dark brown. The precipitate was filtered and washed three times with water and dried in vacuo (3 mmHg) in the atmosphere of P$_2$O$_5$ to obtain 1.96 g (70% yield) of iodine-bridge bonded dimer [Pt(NH$_3$)I$_2$]$_2$. 1.86 g (2 mmol) of [Pt(NH$_3$)I$_2$]$_2$ was suspended in 50 mL of distilled water which had been deairated. Then, 0.6 mL (6 mmol) of cyclopenthylamine

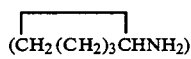

was added and stirred at the room temperature (25° C.) for 12 hours to produce 1.65 g (75% yield) of yellow mixed amine-platinum intermediate

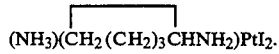

1.653 g (3.0 mmol) of the resulted yellow mixed amine-platinum intermediate

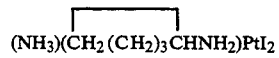

and 0.935 g (3.0 mmol) of Ag$_2$SO$_4$ were reacted as described in Example 1 to obtain aqueous solution of

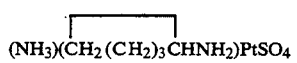

and this solution was gradually added to the 100 mL solution in which 0.95 g (3.0 mmol) of [(CH$_3$)$_2$C=C(COO)$_2$Ba].2H$_2$O was dissolved and stirred for 2 hours. After filtering off the white precipitate, the filtrate was dried under reduced pressure (3 mmHg) and recrystallized in 10 mL of methanol to obtain yellow platinum complex

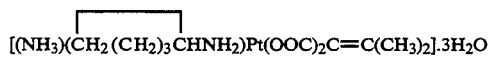

with 87.2% yield.

m.p.: 154° C. (decomp.) Elemental Analysis (%) for (C$_{11}$H$_{20}$N$_2$O$_4$)Pt(3H$_2$O) Found: C, 26.4; H, 3.98; N, 5.60 Calcd.: C, 26.8; H, 5.31; N, 5.68 IR bands (KBr;cm$^{-1}$); 810(m), 1111(m), 1362(s), 1443(m), 1603(s), 2870(m), 2953(m), 3100(s), 3216(s), 3462(m)

EXAMPLE 12

Preparation of

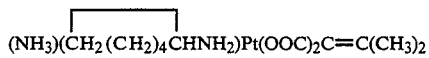

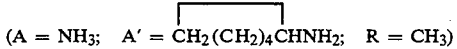

Following the procedure of Example 11 and using the same equivalent of cyclohexylamine instead of cyclopenthylamine, the platinum complex of

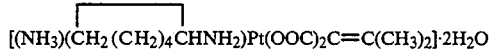

was obtained in 72.6% yield.

m.p.: 142° C. (decomp.) Elemental Analysis (%) for (C$_{12}$H$_{22}$N$_2$O$_4$)Pt(2H$_2$O) Found: C, 29.5; H, 4.94; N, 5.46 Calcd.: C, 29.5; H, 5.35; N, 5.72 IR bands (KBr;cm$^{-1}$); 814(m), 1109(m), 1372(s), 1445(m), 1607(s), 1640(s), 2859(m), 2928(s), 3113(m), 3218(m)

EXAMPLE 13

Preparation of

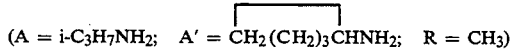

Following the procedure of Example 11 and using the same equivalent of isopropylamine instead of ammonia, the platinum complex of

was obtained in 64.5 yield.

m.p.: 164° C. (decomp.) Elemental Analysis (%) for (C$_{14}$H$_{26}$N$_2$O$_4$)Pt(4H$_2$O) Found: C, 29.5; H, 4.12; N, 5.99 Calcd.: C, 30.4; H, 6.19; N, 5.06 IR bands (KBr;cm$^{-1}$); 808(m), 1022(m), 1229(m), 1254(m), 1368(s), 1620(s), 2928(s), 3108(s), 3198(s), 3439(m)

EXAMPLE 14

Preparation of

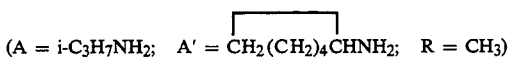

Following the procedure of Example 11 and using the same equivalent of isopropylamine and cyclohexylamine instead of ammonia and cyclopenthylamine respectively, the platinum complex of

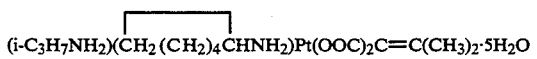

was obtained in 70.1% yield.

m.p.: 146° C. (decomp.) Elemental Analysis (%) for $(C_{15}H_{28}N_2O_4)Pt(5H_2O)$ Found: C, 30.0; H, 4.72; N, 5.84 Calcd.: C, 30.7; H, 6.54; N, 4.78 IR bands (KBr;cm$^{-1}$); 737(m), 777(m), 1113(m), 1364(s), 1402(sh), 1555(s), 1642(m), 2930(m), 3235(m), 3395(m)

EXAMPLE 15

Preparation of
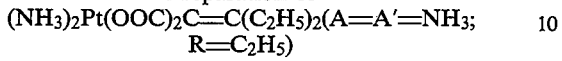
$(NH_3)_2Pt(OOC)_2C=C(C_2H_5)_2$ (A=A'=NH$_3$; R=C$_2$H$_5$)

Following the procedure of Example 1 and using $(C_2H_5)_2C=C(COOC_2H_5)_2$ instead of a malonic acid derivative, $(CH_3)_2C=C(CCOC_2H_5)_2$, the platinum complex of $[(NH_3)_2Pt(OOC)_2C=C(C_2H_5)_2]\cdot 2H_2O$ was obtained in 71.9% yield.

m.p.: 159° C. (decomp.) Elemental Analysis (%) for $(C_8H_{16}N_2O_4)Pt(2H_2O)$ Found: C, 22.5; H, 4.15; N, 6.16 Calcd.: C, 22.1; H, 4.63; N, 6.43 IR bands (KBr;cm$^{-1}$); 698(m), 808(m), 885(m), 1125(m), 1258(sh), 1370(s), 1462(sh), 1609(s), 2969(m), 3102(s), 3237(s)

EXAMPLE 16

Preparation of

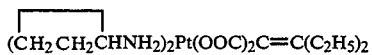
$(CH_2CH_2CHNH_2)_2Pt(OOC)_2C=C(C_2H_5)_2$

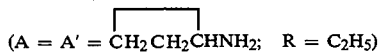
(A = A' = CH$_2$CH$_2$CHNH$_2$; R = C$_2$H$_5$)

Following the procedure of Example 15 and using the same equivalent of cyclopropylamine instead of ammonia, the platinum complex of

$[(CH_2CH_2CHNH_2)_2Pt(OOC)_2C=C(C_2H_5)_2]\cdot 2H_2O$ was obtained in 76.2% yield.

m.p.: 128° C. (decomp.) Elemental Analysis (%) for $(C_{14}H_{24}N_2O_4)Pt(2H_2O)$ Found: C. 32.1; H, 4.72; N, 5.41 Calcd.: C, 32.6; H, 5.47; N, 5.43 IR bands (KBr;cm$^{-1}$); 810(m), 1022(m), 1123(m), 1258(sh), 1372(s), 1460(sh), 1624(s), 2971(m), 3098(s), 3204(s), 3445(m)

EXAMPLE 17

Preparation of $[t(\pm)\text{-}NH_2CH(CH_2)_4CHNH_2]Pt(OOC)_2C=C(C_2H_5)_2$

(AA' = t(±)-NH$_2$CH(CH$_2$)$_4$CHNH$_2$; R = C$_2$H$_5$)

Following the procedure of Example 15 and using the same equivalent of trans(±)-1,2-diaminocyclohexane instead of ammonia, the platinum complex of

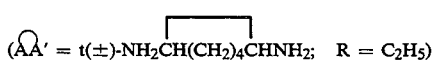
$\{[t(\pm)\text{-}NH_2CH(CH_2)_4CHNH_2]Pt(OOC)_2C=C(C_2H_5)_2\}\cdot 2H_2O$ was obtained in 79.0% yield.

m.p.: 178° C. (decomp.) Elemental Analysis (%) for $(C_{14}H_{24}N_2O_4)Pt(2H_2O)$ Found: C, 32.6; H, 5.28; N, 5.31 Calcd.: C, 32.6; H, 5.47; N, 5.43 bands (KBr;cm$^{-1}$); 708(m), 812(m), 1177(m), 1256(sh), 1350(s), 1454(sh), 1636(s), 2942(s), 3094(s), 3206(s)

EXAMPLE 18

Preparation of

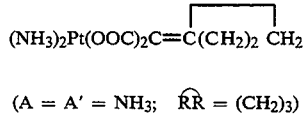
$(NH_3)_2Pt(OOC)_2C=C(CH_2)_2CH_2$ (A = A' = NH$_3$; RR = (CH$_2$)$_3$)

Following the procedure of Example 1 and using

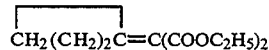
$CH_2(CH_2)_2C=C(COOC_2H_5)_2$ instead of a malonic acid derivative, $(CH_3)_2C=C(COOC_2H_5)_2$, the platinum complex of

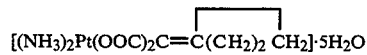
$[(NH_3)_2Pt(OOC)_2C=C(CH_2)_2CH_2]\cdot 5H_2O$ was obtained in 71.3% yield.

m.p.: 159° C. (decomp.) Elemental Analysis (%) for $(C_7H_{12}N_2O_4)Pt(5H_2O)$ Found: C, 17.7; H, 3.30; N, 7.41 Calcd.: C, 17.8; H, 4.68; N, 5.91 IR bands (KBr;cm$^{-1}$); 743(m), 829(m), 963(m), 1298(m), 1356(s), 1387(s), 1618(s), 1661(s), 3100(s), 3264(s), 3324(s), 3488(s)

EXAMPLE 19

Preparation of

$(CH_2CH_2CHNH_2)_2Pt(OOC)_2C=C(CH_2)_2CH_2$

(A = A' = CH$_2$CH$_2$CHNH$_2$; RR = (CH$_2$)$_3$)

Following the procedure of Example 18 and using the same equivalent of cyclopropylamine instead of ammonia, the platinum complex of

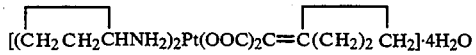
$[(CH_2CH_2CHNH_2)_2Pt(OOC)_2C=C(CH_2)_2CH_2]\cdot 4H_2O$ was obtained in 72.7% yield.

m.p.: 154° C. (decomp.) Elemental Analysis (%) for $(C_{13}H_{20}N_2O_4)Pt(4H_2O)$ Found: C, 28.7; H, 4;64; N, 5.86 Calcd.: C, 29.2; H, 5.27; N, 5.23 IR bands (KBr;cm$^{-1}$); 745(m), 826(m), 934(m), 1022(m), 1385(s), 1622(s), 3108(s), 3202(s), 3424(m)

EXAMPLE 20

Preparation of

$[t(\pm)\text{-}NH_2CH(CH_2)_4CHNH_2]Pt(OOC)_2C=C(CH_2)_2CH_2$

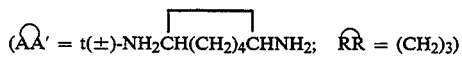
(AA' = t(±)-NH$_2$CH(CH$_2$)$_4$CHNH$_2$; RR = (CH$_2$)$_3$)

Following the procedure of Example 18 and using the same equivalent of trans($\pm$)-1,2-diaminocyclohexane instead of ammonia, the platinum complex of

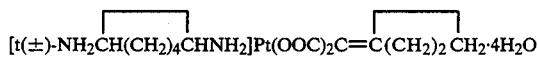

was obtained in 76.4% yield.

m.p.: 183° C. (decomp.) Elemental Analysis (%) for ($C_{13}H_{20}N_2O_5$)Pt(4$H_2O$) Found: C, 28.8; H, 4.71; N, 5.87 Calcd.: C, 29.2; H, 5.27; N, 5.23 IR bands (KBr;$cm^{-1}$); 745(m), 808(m), 961 (m), 1067(m), 1179(m), 1372(s), 1404(s), 1617(s), 1661(s), 2861(m), 2938(m), 3096(s), 3187(s), 3449(m)

EXAMPLE 21

Preparation of

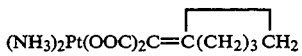

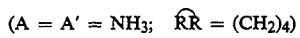

Following the procedure of Example 1 and using

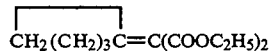

instead of a malonic acid derivative, ($CH_3$)$_2$C=C(COO$C_2H_5$)$_2$, the platinum complex of

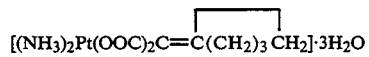

was obtained in 63.2% yield.

m.p.: 182° C. (decomp.) Elemental Analysis (%) for ($C_8H_{14}N_2O_4$)Pt(3$H_2O$) Found: C, 21.1; H, 3.60; N, 6.69 Calcd.: C, 21.3; H, 4.46; N, 6.21 IR bands (KBr;$cm^{-1}$); 754(m), 812(m), 905(m), 1051 (re), 1350(s), 1426(sh), 1559(s), 2959(m), 3237(s), 3459(m)

EXAMPLE 22

Preparation of

Following the procedure of Example 21 and using the same equivalent of cyclopropylamine instead of ammonia, the platinum complex of

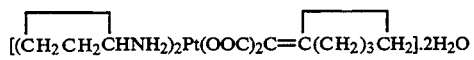

was obtained in 61.6% yield.

m.p.: 112° C. (decomp.) Elemental Analysis (%) for ($C_{14}H_{22}N_2O_4$)Pt(2$H_2O$) Found: C, 32.7; H, 5.30; N, 5.49 Calcd.: C, 32.8; H, 5.10; N, 5.46 IR bands (KBr;$cm^{-1}$); 748(m), 828(m), 1024(m), 1123(m), 1213(m), 1339(s), 1383(m), 1615(s), 2962(m), 3388(s), 3447(m)

EXAMPLE 23

Preparation of

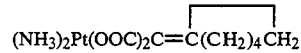

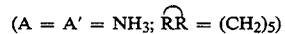

Following the procedure of Example 1 and using

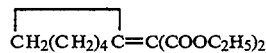

instead of a malonic acid derivative, ($CH_3$)$_2$C=C(COO$C_2H_5$)$_2$, the platinum complex of

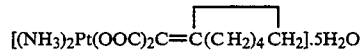

was obtained in 82.1% yield.

m.p.: 145° C. (decomp.) Elemental Analysis (%) for ($C_9H_{16}N_2O_4$)Pt(5$H_2O$) Found: C, 21.6; H, 3.57; N, 6.73 Calcd.: C, 22.4; H, 5.00; N, 5.80 IR bands (KBr;$cm^{-1}$); 696(m), 789(m), 924(m), 1113(m), 1372(s), 1601(s), 2851(m), 2940(m), 3088(s), 3167(s), 3273(s), 3470(m)

EXAMPLE 24

Preparation of

Following the procedure of Example 23 and using the same equivalent cyclopropylamine instead of ammonia, the platinum complex of

was obtained in 72.3% yield.

m.p.: 136° C. (decomp.) Elemental Analysis (%) for ($C_{15}H_{24}N_2O_4$)Pt(2$H_2O$) Found: C, 34.6; H, 4.81; N, 5.58 Calcd.: C, 34.2; H, 5.35; N, 5.31 IR bands (KBr;$cm^{-1}$); 646(m), 826(m), 1022(m), 1252(m), 1375(s), 1397(s), 1634(s), 2932(m), 3090(s), 3202(s)

EXAMPLE 25

Preparation of

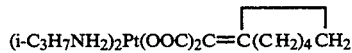

Following the procedure of Example 23 and using the same equivalent of isopropylamine instead of ammonia, the platinum complex of

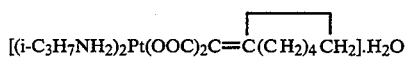

was obtained in 82.6% yield.

m.p.: 167° C. (decomp.) Elemental Analysis (%) for $(C_{15}H_{28}N_2O_4)Pt(2H_2O)$ Found: C, 34.1; H, 5.94; N, 5.14 Calcd.: C, 33.9; H, 6.07; N, 5.27 IR bands (KBr;cm$^{-1}$); 791(m), 808(m), 1117(m), 1254(m), 1385(s), 1576(s), 1634(s), 2930(m), 2971(m), 3129(m) 3189(m), 3466(m)

EXAMPLE 26

Preparation of

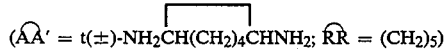

Following the procedure of Example 23 and using the same equivalent of trans($\pm$)-1,2-diaminocyclohexane instead of ammonia, the platinum complex of

was obtained in 74.9% yield.

m.p.: 189° C. (decomp.) Elemental Analysis (%) for $(C_{15}H_{24}N_2O_4)Pt(2H_2O)$ Found: C, 34.2; H, 5.13; N, 5.37 Calcd.: C, 34.2; H, 5.35; N, 5.31 IR bands (KBr;cm$^{-1}$); 791(m), 806(m), 1065(m), 1227(m), 1250(m), 1360(s), 1445(m), 1622(s), 2855(m), 2924(s) 3111(m), 3216(m), 3439(m)

EXAMPLE 27

Preparation of

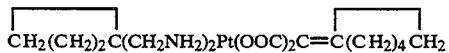

Following the procedure of Example 23 and using the same equivalent of 1,1-cyclobutanedimethaneamine instead of ammonia, the platinum complex of

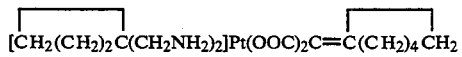

was obtained in 83.8% yield.

m.p.: 201° C. (decomp.) Elemental Analysis (%) for $(C_{15}H_{24}N_2O_4)Pt$ Found: C, 36.9; H, 4.86; N, 6.12 Calcd.: C, 36.7; H, 4.92; N, 5.70 IR bands (KBr;cm$^{-1}$); 787(m), 810(m), 1003(m), 1227(m), 1252(m), 1314(m), 1362(s), 1445(m), 1638(s), 2857(m) 2926(m), 3127(m), 3233(m), 3401(m)

EXAMPLE 28

Preparation of

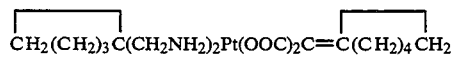

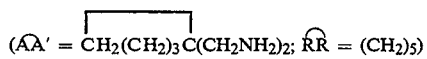

Following the procedure of Example 23 and using the same equivalent of 1,1-cyclopentanedimethaneamine instead of ammonia, the platinum complex of

was obtained in 90.1% yield.

m.p.: 192° C. (decomp.) Elemental Analysis (%) for $(C_{16}H_{26}N_2O_4)Pt(H_2O)$ Found: C, 36.7; H, 5.06; N, 5.75 Calcd.: C, 36.7; H, 5.39; N, 5.35 IR bands (KBr;cm$^{-1}$); 810(m), 1019(m), 1221(m), 1252(m), 1327(m), 1360(s), 1447(m), 1644(s), 2868(m) 2936(s), 3117(m), 3221(s)

EXAMPLE 29

Preparation of

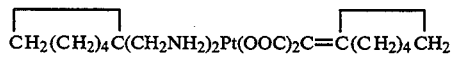

Following the procedure of Example 23 and using the same equivalent of 1,1-cyclohexanedimethaneamine instead of ammonia, the platinum complex of

was obtained in 89.3% yield.

m.p.: 198° C. (decomp.) Elemental Analysis (%) for $(C_{17}H_{28}N_2O_4)Pt(H_2O)$ Found: C, 38.5; H, 5.50; N, 5.57 Calcd.: C, 38.0; H, 5.62; N, 5.21 IR bands (KBr;cm$^{-1}$); 694(m), 810(m), 920(m), 1036(m), 1225(m), 1352(s), 1454(m), 1636(s), 2851(m), 2924(s) 3127(m), 3218(m)

EXAMPLE 30

Preparation of

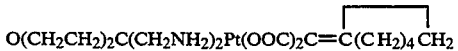

Following the procedure of Example 23 and using the same equivalent of tetrahydro-4H-pyran-4,4-dimethaneamine instead of ammonia, the platinum complex of

was obtained in 85.6% yield.

m.p.: 168° C. (decomp.) Elemental Analysis (%) for ($C_{16}H_{26}N_2O_5$)Pt($2H_2O$) Found: C, 34.9; H, 5.26; N, 5.08 Calcd.: C, 34.5; H, 5.42; N, 5.02 IR bands (KBr;cm$^{-1}$); 808(m), 1026(m), 1100(m), 1229(m), 1250(sh), 1366(s), 1603(s), 1630(s), 2853(m), 2926(s) 3110(s), 3189(s), 3443(s)

EXAMPLE 31

Preparation of

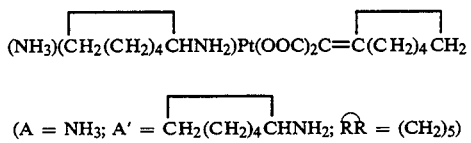

Following the procedure of Example 12 and using the same equivalent of $CH_2(CH_2)_4C=C(COOC_2H_5)_2$ instead of a malonic acid derivative, $(CH_3)_2C=C(COOC_2H_5)_2$, the platinum complex of

was obtained in 71.5% yield.

m.p.: 180° C. (decomp.) Elemental Analysis (%) for ($C_{15}H_{26}N_2O_4$)Pt($2H_2O$) Found: C, 34.3; H, 6.19; N, 5.17 Calcd.: C, 34.0; H, 5.71; N, 5.29 IR bands (KBr;cm$^{-1}$); 810(m), 1229(m), 1254(m), 1346(s), 1366(s), 1449(m), 1603(s), 2853(m), 2926(s), 3221(s) 3464(m )

IN VIVO TEST AGAINST LEUKEMIA L1210 CELL LINE

The platinum complexes of the present invention were evaluated for antitumor activity against murine Leukemia L1210 cell line, according to the standard method of Goldin et al. (*Europ. J. Cancer.* 17, 129 (1981)). Each test group consisted of 8 BDF$_1$ mice of 6 to 8 weeks old. 10$^6$ cells of Leukemia L1210 were implanted by intraperitoneal injection to each mouce, and the platinum test compounds dissolved in 0.9% physiological saline solution were administered intraperitoneally on days 1, 5 and 9 at various doses in the range of 10-40 mg/Kg. Table 1 presents the result of the observation on Increased Life Span (%) and number of survived animals on day 60. From Table 1, it is clearly shown that the antitumor activity of the platinum complexes of the present invention is superior to that of cisplatin or carboplatin.

TABLE 1

| Antitumor Activity Against Murine L1210 Leukemia | | | |
|---|---|---|---|
| Compound of | Dose (mg/kg) | Increased Life | Number of Survived Animals on day 60 |
| Example 5 | 40 | 76.6 | 0 |
|  | 10 | 44.1 | 0 |
| Example 12 | 40 | >233.3 | 8/8 |
|  | 10 | >130.0 | 3/8 |
| Example 18 | 40 | 128 |  |
|  | 10 | 39 |  |
| Example 19 | 10 | >278.4 | 7/8 |
| Example 22 | 30 | >241.8 | 5/8 |
| Example 24 | 40 | >261.1 | 5/8 |
|  | 10 | 88.4 | 0 |
| Cisplatin | 4 | 84.5 | 0 |
|  | 1 | 38.6 | 0 |
| Carboplatin | 40 | 59.3 | 0 |
|  | 20 | 46.9 | 0 |

What is claimed is:

1. A platinum complex represented by the following formula I:

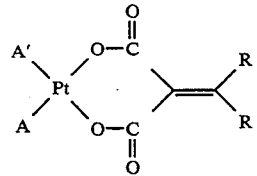

wherein R is methyl or ethyl, or these two R groups combine to form propylene, butylene, or pentylene; A and A' are same or different from each other and are selected from the group consisting of ammonia, methylamine, isopropylamine, cyclopropylamine, cyclobutylamine, and cyclohexylamine in the case of being monodentate neutral ligand, or A and A' combine to form chelating amine such as ethylenediamine, trans(±)-1,2-diaminocyclohexane, 2,2-dimethyl-1,3-propanediamine, 1,1-cyclobutanedimethaneamine, 1,1-cyclopentanedimethaneamine, 1,1-cyclohexanedimethaneamine, or tetrahydro-4H-pyran-4,4-dimethaneamine.

* * * * *